United States Patent
Krause et al.

(10) Patent No.: US 6,593,270 B1
(45) Date of Patent: *Jul. 15, 2003

(54) MOLDINGS BASED ON PYROGENIC SILICON DIOXIDE

(75) Inventors: Helmfried Krause, Rodenbach (DE); Hermanus Lansink Rotgerink, Glattbach (DE); Oliver Feuer, Nidderau (DE); Thomas Tacke, Paducah, KY (US); Peter Panster, Rodenbach (DE)

(73) Assignee: Degussa AG, Dusseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/187,420

(22) Filed: Nov. 6, 1998

(30) Foreign Application Priority Data

Nov. 13, 1997 (DE) .......................... 197 50 238

(51) Int. Cl.$^7$ ........................... B01J 23/44; B01J 23/60; B01J 23/58; B01J 23/52

(52) U.S. Cl. ...................... 502/328; 502/330; 502/339; 423/335

(58) Field of Search ................. 502/326, 328, 502/330, 339, 232, 240, 243; 423/335

(56) References Cited

U.S. PATENT DOCUMENTS

| 4,482,642 A | * | 11/1984 | Ettlinger et al. | |
| 5,021,378 A | | 6/1991 | Deller | |
| 5,086,031 A | | 2/1992 | Deller | |
| 5,250,487 A | * | 10/1993 | Wirtz et al. | 502/243 |
| 5,292,931 A | | 3/1994 | Wirtz et al. | |
| 5,559,071 A | * | 9/1996 | Abel et al. | 502/326 |
| 5,591,873 A | | 1/1997 | Bankmann et al. | |
| 5,610,116 A | * | 3/1997 | Werdecker et al. | |
| 5,685,932 A | | 11/1997 | Stohr et al. | |
| 5,776,240 A | * | 7/1998 | Deller et al. | 106/482 |
| 5,808,136 A | * | 9/1998 | Tacke et al. | 560/243 |
| 5,858,906 A | * | 1/1999 | Deller et al. | 502/170 |
| 6,207,610 B1 | | 3/2001 | Krause et al. | |
| 6,316,383 B1 | * | 11/2001 | Tacke et al. | 106/482 |

FOREIGN PATENT DOCUMENTS

| DE | 3132674 A1 | 3/1983 |
| DE | 3406185 A1 | 9/1985 |
| DE | 3912504 | 10/1990 |
| DE | 3912504 A1 | 10/1990 |
| DE | 41 42 902 | 6/1993 |
| DE | 19619961 A1 | 11/1997 |
| EP | 0037220 | 10/1981 |
| EP | 0167324 | 1/1986 |
| EP | 0327722 | 8/1989 |
| EP | 0519435 | 12/1992 |
| EP | 0519435 A1 | 12/1992 |
| EP | 0725037 | 8/1996 |
| EP | 0807615 | 11/1997 |
| EP | 0 807 615 | 11/1997 |

* cited by examiner

Primary Examiner—Tom Dunn
Assistant Examiner—Christina Ildebrando
(74) Attorney, Agent, or Firm—Pillsbury Winthrop LLP

(57) ABSTRACT

Moldings based on pyrogenic silicon dioxide with a pore volume of 0.5 to 1.8 ml/g are prepared by homogenizing pyrogenic silicon dioxide with methylhydroxyethyl cellulose, wax and polyethylene glycol with the addition of water, subjecting this mixture to a compounding and shaping process, extruding, optionally cutting the extrudate to the desired length using a cutting device, drying at a temperature of 70° to 150° C. and conditioning for a period of 30 minutes to 10 hours at a temperature of 400° to 1200° C. The moldings may be used as catalysts or catalyst supports for the preparation of vinyl acetate monomer, the hydration of ethylene and the hydration of propylene.

8 Claims, No Drawings

MOLDINGS BASED ON PYROGENIC SILICON DIOXIDE

CROSS REFERENCE TO RELATED APPLICATIONS

The present application claims priority under 35 U.S.C. §119 to application 19750238.5, filed in Germany on Nov. 13, 1997.

FIELD OF THE INVENTION

The invention relates to moldings based on pyrogenic silicon dioxide, a process for their preparation and their use as catalyst supports or catalysts.

BACKGROUND OF THE INVENTION

Pyrogenic silicon dioxides are characterised by extreme fineness and a correspondingly high specific surface area, very high purity, spherical particle shapes and the lack of pores. Due to these properties, pyrogenic oxides are becoming increasingly important as supports for catalysts (D. Koth, H. Ferch, Chem. Ing. Techn. 52, 628 (1980)).

Since pyrogenic oxides are particularly finely divided, there are some problems involved when shaping them to provide catalyst supports or catalysts.

DE-A 31 32 674 discloses a process for preparing moldings from pyrogenic oxides in which silica sol is used as a binder.

DE-A 34 06 185 discloses a process for preparing moldings in which a sintered glass powder is used as binder and glycerine is used as lubricant.

DE-B 21 00 778 discloses granules based on pyrogenic silicon dioxides which can be used as catalyst supports for preparing vinyl acetate monomer.

DE-A 39 12 504 discloses a process for preparing moldings in which aluminium stearate, magnesium stearate and/or graphite is used as lubricant and urea and methyl cellulose are used as pore producers.

The known moldings prepared using magnesium stearate are sold as Aerosil tablets No. 350 by Degussa AG, Germany. They contain about 0.4 wt. % of Mg.

EP-B 0 519 435 discloses compressing $SiO_2$ using binders to provide a support, calcining the support obtained and washing the calcined support particles with acid until no further cations from the binder are liberated.

The known processes have the disadvantage that the moldings obtained do not have the optimum properties required, such as, for example, high purity, high activity, high selectivity, high product yield and high stability, for use in specific catalytic reactions such as, for example, the production of vinyl acetate from ethylene, acetic acid and oxygen, the hydration of ethylene to give ethanol or the hydration of propylene to give isopropanol.

The earlier, but not previously published, patent application DE 196 19 961.1-41 describes moldings based on pyrogenic silicon dioxide with the following physico-chemical characteristics:

| External diameter | 0.8–20 mm |
| --- | --- |
| BET surface area | 30–400 m$^2$/g |
| Pore volume | 0.5–1.3 ml/g |
| Breaking strength | 10–250 N |
| Composition | >99.8 wt. % $SiO_2$ |
| Other constituents | <0.2 wt. % |
| Abrasion | <5 wt. % |
| Bulk density | 350–750 g/l |

SUMMARY OF THE INVENTION

The present invention provides moldings based on pyrogenic silicon dioxide which are characterised by having a pore volume of 0.5 to 1.8 ml/g, preferably 1.31 to 1.8 ml/g.

The moldings according to the invention may have an external diameter of 0.8 to 20 mm, a BET surface area of 30 to 400 m$^2$/g and a fracture strength of 7 to 250 N.

The $SiO_2$ fraction in the moldings according to the invention is preferably greater than 99.0 wt. %. The proportion of other constituents may be less than 0.2 wt. %. Moldings according to the invention may therefore be regarded as containing no binder. The abrasion may be less than 5 wt. %. The compacted density may be 300 to 750 g/l.

The invention also provides a process for preparing moldings based on pyrogenic silicon dioxide with a pore volume of 0.5 to 1.8 ml/g, which is characterised in that pyrogenic silicon dioxide is homogenised with methylhydroxyethyl cellulose, wax and polyethylene glycol with the addition of water, subjected to a compounding and shaping process, extruded, optionally cutting the extrudate to the desired length using a cutting device, drying at a temperature of 70° to 150° C. and conditioning for a period of 30 minutes to 10 hours at a temperature of 400° to 1200° C.

Any compounders, mixers or mills which enable efficient homogenisation and compacting of the material being mixed such as, for example, blade, fluidised bed, propeller or air-flow mixers are suitable for performing the process according to the invention. Mixers with which additional compaction of the material being mixed is possible such as, for example, plough-bar mixers, pan mills or ball mills are particularly suitable. Mixing and compounding may also take place, however, directly in an extruder. The extrudates may also be prepared in single or twin-screw extruders, compression extruders or in compactors. The moldings according to the invention are preferably prepared using extruders.

In a particular embodiment of the invention, the mixture may have the following composition prior to compression:

| | |
| --- | --- |
| 50–90 wt. % | silicon dioxide, preferably 65–85 wt. %; |
| 0.1–20 wt. % | methylhydroxyethyl cellulose, preferably 5–15 wt. %; |
| 0.1–15% | wax, preferably 5–12 wt. %, |
| 0.1–15% | polyethylene glycol, preferably 5–10 wt. %. |

The moldings may have a variety of shapes such as, for example, cylinders, spheres or rings with an external diameter of 0.8 to 20 mm. The moldings are conditioned at 400° to 1200° C. for 30 minutes to 10 hours. The fracture strength, the specific total surface area and the pore volume can be adjusted to a certain extent by varying the amounts of starting compounds and the pressure applied.

Moldings according to the invention may be used either directly as a catalyst or as a catalyst support. In the latter case the moldings are placed in contact with a catalytically active substance after their preparation and optionally activated by means of appropriate post-treatment.

In particular, the moldings made from pyrogenic silicon dioxide may be used as supports for the catalyst during the preparation of vinyl acetate monomer from ethylene, acetic acid and oxygen and as a catalyst support in olefin hydration processes, for example during the preparation of ethanol and isopropanol.

Moldings according to the invention have the following advantages:

In comparison with moldings in accordance with document DE-A 39 12 504, moldings according to the invention have no other inorganic constituents apart from silicon dioxide. The known moldings have the disadvantage that they contain about 0.4 wt. % of Mg which is leached out during the process for hydration of olefins.

Moldings according to the invention on the other hand have an improved hydrothermal stability in this type of hydration reaction. In addition, they are very pure and have a high pore volume.

A further advantage is produced from the fact that a larger space/time yield is produced during hydration. During hydration of olefins, the pore volume of the catalyst support plays a very important part. The relatively large pore volume, surprisingly, enables the absorption of more active phase. This results in an increase in the space/time yield.

The invention also provides a supported catalyst for the production of vinyl acetate monomer (VAM), which contains, on a support (molding), as catalytically active components, palladium and/or its compounds and alkali metal compounds, and also gold and/or its compounds (Pd/alkali metal/Au system) or cadmium and/or its compounds (Pd/alkali metal/Cd system) or barium and/or its compounds (Pd/alkali metal/Ba system) or palladium, alkali metal compounds and mixtures of gold and/or cadmium and/or barium, which is characterised in that the support is a molding in accordance with the invention. Potassium compounds such as e.g. potassium acetate are preferred as alkali metal compounds.

The catalytically active components may be present in the following systems:

Pd/Au/alkali metal compounds

Pd/cd/alkali metal compounds

Pd/Ba/alkali metal compounds

The supported catalysts according to the invention are used for the production of vinyl acetate monomer. For this, ethylene, acetic acid and molecular oxygen or air are reacted in the gas phase, optionally with the addition of inert gases, at temperatures between 100° and 250° C. and usually under elevated pressure in the presence of the supported catalyst according to the invention.

A production process of this type is known from the documents DE 16 68 088, U.S. Pat. No. 4,048,096, EP-A 0 519 435, EP-A 0 634 208, EP-A 0 723 810, EP-A 0 634 209, EP-A 0 632 214 and EP-A 0 654 301. These patents also disclose a process for preparing supported catalysts. Depending on the embodiment, supported catalysts with homogeneous distribution of noble metal over the cross section of the support and with a relatively well-defined shell profile are obtained.

The invention also provides a process for preparing supported catalysts for the production of vinyl acetate monomer by soaking, spraying, moistening, immersing or precipitating the Pd, Au, Cd, Ba metal compounds, optionally reducing the reducible metal compounds applied to the support, washing to remove optionally present chloride, impregnating with alkali metal acetates or alkali metal compounds which are completely or partly converted into alkali metal acetates under the reaction conditions for the production of vinyl acetate monomer, in a suitable sequence, which is characterised in that the support is a molding in accordance with the invention.

The invention also provides a process for preparing supported catalysts for the production of vinyl acetate monomer by impregnating the support with a basic solution and a solution containing gold and palladium salts, wherein the impregnation steps are performed at the same time or in sequence, with or without intermediate drying, washing the support to remove optionally present chloride and reducing the insoluble compounds precipitated onto the support before or after washing, drying the catalyst precursor obtained in this way, and impregnating with alkali metal acetates or alkali metal compounds which are completely or partly converted into alkali metal acetates under the reaction conditions for the production of vinyl acetate monomer, which is characterised in that the support is a molding in accordance with the invention.

The supported catalysts according to the invention may be used to prepare unsaturated esters from olefins, acids and oxygen in the gas phase.

Catalysts according to the invention containing the Pd/alkali metal/Au catalyst system are usually obtained by impregnating the support with a basic solution and a solution containing gold and palladium salts, wherein the impregnation steps are performed simultaneously or in sequence, with or without intermediate drying. Then the support is washed to remove optionally present chloride. Before or after washing, the insoluble noble metal compounds precipitated onto the support are reduced. The catalyst precursor obtained in this way is dried and impregnated with alkali metal acetates or alkali metal compounds which are converted entirely or partly into alkali metal acetates under the reaction conditions for the production of vinyl acetate monomer, in order to activate the catalyst. The noble metal in Pd/Au catalysts is generally present in the form of an outer shell on the support.

In the case of Pd/alkali metal/Ba catalysts, the metal salts are applied by soaking, spraying, moistening, immersing or precipitating (EP 0 519 436). The same methods are also known for Pd/alkali metal/Cd catalysts (U.S. Pat. Nos. 4,902,823, 3,393,199, 4,668,819).

Depending on the catalyst system used, the supported catalyst may then be reduced.

Reduction of the catalyst may be performed in the aqueous phase or in the gas phase. Formaldehyde or hydrazine, for example, are suitable for reducing in the aqueous phase. Reduction in the gas phase may be performed with hydrogen and/or forming gas (95 vol. % $N_2$ plus 5 vol. % $H_2$), ethylene or nitrogen-diluted ethylene. According to EP 0 634 209, reduction with hydrogen is performed at temperatures between 40 and 260° C., preferably between 70 and 200° C. According to EP-A 0 723 810, reduction with forming gas (95 vol. % $N_2$ and 5 vol. % $H_2$) is performed at temperatures between 300 and 550° C., preferably between 350 and 500° C. Frequently, however, the catalyst is reduced directly with ethylene in the production reactor after activation with alkali metal acetate.

In the production process, the catalyst is loaded with reactants only slowly. During this start up phase, the activity of the catalyst increases and probably reaches its ultimate level only after several days or weeks.

An object of the present invention is to provide a supported catalyst for the production of vinyl acetate monomer which has a higher activity than known catalysts with the same or improved selectivity.

The invention provides a supported catalyst which contains, on the silicon dioxide support according to the invention, as catalytically active components, palladium and/or its compounds and alkali metal compounds, and also gold and/or its compounds (Pd/alkali metal/Au system) or cadmium and/or its compounds (Pd/alkali metal/Cd system) or barium and/or its compounds (Pd/alkali metal/Ba system) or palladium, alkali metal compounds and mixtures of gold and/or cadmium and/or barium and a process for its preparation.

The moldings according to the invention based on pyrogenic silicon dioxide are suitable as support material for the catalyst. It is important that the catalyst support retains its mechanical strength under the reaction conditions of the catalytic process, in particular under the effect of acetic acid.

Moldings according to the invention may be produced as extruded moldings, tablets, rings or in any other shape conventionally used for fixed bed catalysts.

In the following, the preparation of supported catalysts with the system Pd/alkali metal/Au on the moldings according to the invention is described in more detail.

The moldings according to the invention are impregnated with a solution which contains palladium and gold. The moldings according to the invention are impregnated with a basic solution which may contain one or more basic compounds, either at the same time as the noble metal-containing solution or in any sequence. The basic compound or compounds are used to convert the palladium and gold into their hydroxides.

The compounds in the basic solution may consist of alkali metal hydroxides, alkali metal bicarbonates, alkali metal carbonates, alkali metal silicates or mixtures of these substances. Potassium hydroxide and/or sodium hydroxide are preferably used.

Palladium chloride, sodium or potassium palladium chloride or palladium nitrate, for example, may be used as a palladium salt to prepare the noble metal-containing solution. Gold(III) chloride and tetrachloroauric(III) acid are suitable as gold salts. Potassium palladium chloride, sodium palladium chloride and/or tetrachloroauric acid are preferably used.

The deposition of the noble metals in the molding has an effect on the impregnation of the molding according to the invention with the basic solution. The basic solution may be placed in contact with the moldings according to the invention either at the same time as the noble metal solution or in any sequence with this solution. In the case of sequential impregnation of the molding according to the invention with the two solutions, an intermediate drying stage may be performed after the first impregnation step.

The molding according to the invention is preferably first impregnated with the basic compound. Subsequent impregnation with the solution containing palladium and gold leads to precipitation of palladium and gold in an outer shell of the molding according to the invention. The reverse sequence of impregnation generally leads to relatively homogeneous distribution of the noble metals over the cross section of the molding according to the invention. Catalysts with defined outer shells can be obtained, however, even when the reverse impregnation sequence is used with appropriate process management (see e.g. U.S. Pat. No. 4,048,096). Catalysts with homogeneous or approximately homogeneous distribution of the noble metal generally have lower activity and selectivity.

Catalysts with shell thicknesses of less than 1 mm, preferably of less than 0.5 mm are particularly suitable. The shell thickness is affected by the amount of basic compound relative to the desired amount of noble metal which is applied to the support material. The higher this ratio, the thinner is the shell which is produced. The ratio between the basic compound and noble metal compounds required for a specific shell thickness depends on the nature of the support material and on the basic compound and noble metal compounds selected. The ratio required is expediently determined by a few preliminary experiments. The shell thickness produced can be determined in a simple way by cutting through the catalyst particles.

The minimum amount of basic compound required is produced from the stoichiometrically calculated amount of hydroxide ions which are required to convert the palladium and gold into hydroxides. As a guideline it may be assumed that the basic compound should be used in a one to tenfold stoichiometric excess for a shell thickness of 0.5 mm.

The moldings according to the invention are coated with the basic compounds and noble metal salts by the process of pore volume impregnation. If intermediate drying is required, the volumes of the two solutions are selected in such a way that each corresponds to about 90 to 100% of the absorption capacity of the moldings according to the invention. If no intermediate drying step is used, then the sum of the individual volumes of the two impregnating solutions should comply with the condition mentioned above, wherein the individual volumes may be in a ratio of 1:9 to 9:1 with respect to each other. A ratio by volume of 3:7 to 7:3, in particular of 1:1, is preferably used. Water is preferably used as solvent in both cases. However appropriate organic or aqueous organic solvents may also be used.

Reaction of the noble metal salt solution with the basic solution to give insoluble noble metal compounds takes place slowly and is generally only concluded after 1 to 24 hours, depending on the method of preparation. Then, the water-insoluble noble metal compounds are treated with a reducing agent. Wet reduction, for example using aqueous hydrazine hydrate, or gas phase reduction using hydrogen, ethylene, forming gas or methanol vapour is then performed. Reduction may take place at ambient temperature or at elevated temperature and under atmospheric or elevated pressure; optionally also with the addition of inert gases.

Before and/or after reduction of the noble metal compounds, any chloride which is present on the support should be removed by thorough washing. After washing, the catalyst should contain less than 500, better less than 200 ppm of chloride.

The catalyst precursor obtained after reduction is dried and then impregnated with alkali metal acetates or alkali metal compounds which are completely or partly converted into alkali metal acetates under the reaction conditions for the production of vinyl acetate monomer. Preferably, they are impregnated with potassium acetate. Again pore volume impregnation is preferably used here. That is to say: the required amount of potassium acetate is dissolved in a solvent, preferably water, the volume of which corresponds approximately to the absorption capacity of the precoated support material for the selected solvent. This volume is approximately equal to the total pore volume of the support material.

The final catalyst is then dried to a residual moisture content of less than 2%. Drying may be performed in air, optionally also under nitrogen as an inert gas.

Supported catalysts with the Pd/alkali metal/Cd or Pd/alkali metal/Ba systems on moldings according to the invention are prepared in accordance with the patents cited above.

For the synthesis of vinyl acetate monomer, it is expedient to coat the catalyst with 0.2 to 4, preferably 0.3 to 3 wt. % of palladium, 0.1 to 2, preferably 0.15 to 1.5 wt. % of gold and 1 to 10, preferably 1.5 to 9 wt. % of potassium acetate, each with respect to the weight of support used. This data applies to the Pd/alkali metal/Au system. In the case of catalyst supports with a bulk density of 500 g/l, this concentration range corresponds to volume related concentrations of 1.0 to 20 g/l of palladium, 0.5 to 10 g/l of gold and 5 to 50 g/l of potassium acetate. To make up the impregnating solutions, the corresponding amounts of palladium and gold compounds are dissolved in a volume of water which corresponds to about 90 to 100% of the water absorption capacity of the particular support material. The same procedure is used for making up the basic solution.

The cadmium content of the Pd/alkali metal/Cd catalysts is generally 0.1 to 2.5 wt. %, preferably 0.4 to 2.0 wt. %.

The barium content of the Pd/alkali metal/Ba catalysts is generally 0.1 to 2.0 wt. %, preferably 0.2 to 1.8 wt. %.

The palladium content of Pd/alkali metal/Cd or Pd/alkali metal/Ba catalysts may be 0.2 to 4 wt. %, preferably 0.3 to 3 wt. % of palladium.

The potassium content of the Pd/alkali metal/Cd or Pd/alkali metal/Ba catalysts is generally 1 to 10 wt. %, preferably 1.5 to 9 wt. %.

The invention also relates to catalytic reactions under hydrothermal conditions, such as e.g. the hydration of olefins to give the corresponding alcohols in the presence of phosphoric acid or another active component, for example a heteropoly acid, wherein the moldings according to the invention are used as catalyst supports.

A process of this type is described, for example, in EP 0 578 441 A2. According to this process, water and ethylene are reacted at temperatures between 225° and 280° C. and pressures between 20 and 240 bar to give ethanol. Here, a molar ratio of water to ethylene in the region 0.15 to 0.5 is used. The catalyst loading, measured as grams of water per ethylene mixture per minute and per milliliter of catalyst may be selected within the range 0.01 to 0.1 g/(min×ml).

Diethylether is produced as a secondary product during this reaction.

The process parameters for preparing ethanol may also be outside the range mentioned above. An example of this can be found in DE-OS 20 15 536 (example 1): The temperature in this case was about 300° C. and the water to ethylene ratio about 0.74 mol/mol, with a total pressure of 70 bar. The essential point here is that the temperature and water vapour pressure must be mutually selected.

The preparation of isopropanol by hydration of propylene takes place under similar conditions. The temperature then however lies in the range between 180° and 225° C. n-propanol is produced as a secondary product during this reaction.

Pellets of synthetic silicon dioxide with a high fracture strength, high porosity and low metallic contamination may be used as catalyst supports for the active component phosphoric acid in accordance with EP 0 578 441 A2. The pores in the support are used to absorb the active component. The average pore radius before use in hydration reactions is in the range between 1 and 50 nm.

In the case of hydration of olefins, phosphoric acid is introduced as an active component into the catalyst support. For this purpose, the support is immersed in and soaked with an aqueous solution of phosphoric acid. Phosphoric acid solutions with 15 to 85 wt. % of phosphoric acid, with respect to the total weight of solution, are used here. Coating with a heteropoly acid as active component is also possible.

A main area of use of the hydration of olefins is the hydration of ethylene to produce ethanol and diethylether and the hydration of propylene to produce isopropanol. The reaction conditions known from the prior art may be used for these reactions.

Silicon dioxides with the physico-chemical characteristics shown in the following Table may be used as pyrogenic silicon dioxide.

|  |  | Aerosil OX 50 | Aerosil 90 | 130 | 150 | 200 | 300 | 380 |
|---|---|---|---|---|---|---|---|---|
| BET surface area | m$^2$/g | 50 ± 15 | 90 ± 15 | 130 ± 25 | 150 ± 15 | 200 ± 25 | 300 ± 30 | 380 ± 30 |
| Average size of primary particles | nm | 40 | 20 | 16 | 14 | 12 | 7 | 7 |
| Compacted density[1] | g/l | ca. 130 | ca. 80 | ca. 50 | ca. 50 | ca. 50 | ca. 50 | ca. 50 |
| Loss on drying[2] (2 hours at 105° C.) | % | <1.5 | <1 | <1.5 | <0.5[7] | <1.5 | <1.5 | <1.5 |
| Loss on ignition[2)5] (2 hours at 1000° C.) | % | <1 | <1 | <1 | <1 | <1 | <2 | <2.5 |
| PH[3] (in 4% strength aqueous dispersion) |  | 3.8–4.8 | 3.6–4.5 | 3.6–4.3 | 3.6–4.3 | 3.6–4.3 | 3.6–4.3 | 3.6–4.3 |
| $SiO_2$ [6] | % | >99.8 | >99.8 | >99.8 | >99.8 | >99.8 | >99.8 | >99.8 |
| $Al_2O_3$ [6] | % | <0.08 | <0.05 | <0.05 | <0.05 | <0.05 | <0.05 | <0.05 |
| $Fe_2O_3$ [6] | % | <0.01 | <0.003 | <0.003 | <0.003 | <0.003 | <0.003 | <0.003 |
| $TiO_2$ [6] | % | <0.03 | <0.03 | <0.03 | <0.03 | <0.03 | <0.03 | <0.03 |
| HCl[6)8] | % | <0.025 | <0.025 | <0.025 | <0.025 | <0.025 | <0.025 | <0.025 |
| Residue after sieving[4] (Mocker's method 45 μm) | % | <0.02 | <0.05 | <0.05 | <0.05 | <0.05 | <0.05 | <0.05 |

[1] from DIN 53 194
[2] from DIN 55 921
[3] from DIN 53 200
[4] from DIN 53 580
[5] with respect to the substance dried for 2 hrs at 105° C.
[6] with respect to the substance ignited for 2 hrs at 1000° C.
[8] HCl is a constituent of the loss on ignition To prepare AEROSIL, a volatile silicon compound is sprayed into an oxyhydrogen gas flame consisting of hydrogen and air. In most cases silicon tetrachloride is produced. This substance hydrolyses under the effect of the water produced in the oxyhydrogen gas reaction to give silicon dioxide and hydrochloric acid. The silicon dioxide, after leaving the flame, is introduced into a so-called coagulation zone where the AEROSIL primary particles and primary aggregates are agglomerated. The product produced in this stage as a type of aerosol is separated from the gaseous accompanying substances in cyclones and then post-treated with moist hot air. As a result of this process, the residual hydrochloric acid content drops to below 0.025%. Since the AEROSIL at the end of this process is produced with a bulk density of only about 15 g/l, a vacuum compaction process follows, by means of which compacted densities of about 50 g/l or above may be produced.

The particle sizes of the products obtained in this way may be varied by varying the reaction conditions, such as for example the flame temperature, the proportion of hydrogen or oxygen, the amount of silicon tetrachloride, the residence time in the flame or the length of the coagulation zone.

The BET surface area is determined in accordance with DIN 66 131 using nitrogen. The pore volume is calculated arithmetically from the sum of the micro, meso and macro pore volumes. The fracture strength is determined by using the breaking strength tester from the Erweka company (model TBH 28).

The micro and meso pores are determined by recording a $N_2$-isotherm and evaluating it in accordance with BET, de Boer and Barret, Joyner, Halenda.

The macro pores are determined using the Hg injection process.

Abrasion is determined by means of the abrasion and friability tester (model TAR) from the Erweka company.

This application is based on priority application DE197 50 238.5, filed Nov. 13, 1997, which entire disclosure is incorporated herein by reference.

DETAILED DESCRIPTION OF THE PREFERRED EMBODIMENTS

EXAMPLE

Example 1

| 69 wt. % | Aerosil 200 |
| 12.5 wt. % | methylhydroxyethyl cellulose |
| 10.2 wt. % | wax |
| 8.3 wt. % | polyethylene glycol | are compacted in a compounder, while adding water. The compounded material is shaped in a single-screw extruder to form extruded moldings and is cut into the desired lengths of 3 to 5 mm with a cutting device. The moldings are dried in a conveyor belt dryer at 90° C. The crude moldings are calcined for 6 hours at 75° C.

The moldings obtained have the following physico-chemical characteristics:

| Dimension of moldings: | |
| --- | --- |
| Diameter (mm) | 3.75 |
| Length (mm) | 4 ± 1 |
| BET surface area (m$^2$/g) | 160 |
| Pore volume (ml/g) | 1.41 |
| Fracture strength (N) | 25 |
| Abrasion (wt. %) | 2.1 |
| Compacted density (g/l) | 348 |
| SiO$_2$ content (wt. %) | 99.85 |

Examples 2 and 3

| 71.4 wt. % | Aerosil 200 |
| 12.9 wt. % | methylhydroxyethyl cellulose |
| 7.1 wt. % | wax |
| 8.6 wt. % | polyethylene glycol | are shaped to give extruded moldings, while adding water, in a twin-screw extruder and are cut into the desired lengths of 3 to 5 mm or 2 to 4 mm, using a cutting device. The moldings are dried at 110° C. in a drying cabinet. The crude moldings are calcined for 6 hours at 750° C.

The moldings obtained have the following physico-chemical characteristics:

| Dimensions of molding: | Example 2 | Example 3 |
| --- | --- | --- |
| Diameter (mm) | 3.7 | 2.65 |
| Length (mm) | 4 ± 1 | 3 ± 1 |
| BET surface area (m$^2$/g) | 160 | 163 |
| Pore volume (ml/g) | 1.46 | 1.54 |
| Fracture strength (N) | 20 | 7 |
| Abrasion (wt. %) | 0.8 | 1.15 |
| Compacted density (g/l) | 327 | 310 |
| SiO$_2$ content (wt. %) | 99.9 | 99.9 |

Example 4

Hydration of ethylene using a known catalyst support.

The catalyst support 350, from Degussa AG, which corresponds to the prior art has a pore volume of 0.8 ml/g. This catalyst support is soaked in a 60 wt. % $H_3PO_4$ solution and then dried. 50 ml of this catalyst is incorporated into a fixed bed reactor and strongly heated at 240° C. under a stream of nitrogen. Then the nitrogen is replaced by a gaseous mixture of ethylene and water. The water throughput is 0.20 g/min, the water/ethylene ratio is 0.27 mol/mol. Analysis of the emerging gases is performed using on-line gas chromatography. To assess the catalytic activity, the ratio of the area of ethanol to ethylene is evaluated. With an average catalyst temperature of 240° C., a ratio of 0.078 is calculated for the catalyst based on the known support 350.

Example 5

Hydration of ethylene using a catalyst support according to the invention.

A $SiO_2$ catalyst support with a pore volume of 1.36 ml/g in accordance with the invention is loaded with $H_3PO_4$ solution in the same way as in example 4 and tested in the same reaction. The water throughput is 0.22 g/min, the water to ethylene ratio is 0.30 mol/mol. With this catalyst on the catalyst support according to the invention, the ratio of areas obtained on a gas chromatogram is 0.103, i.e. it is 32% higher than with the catalyst based on the known support.

What is claimed is:

1. Moldings comprising pyrogenic silicon dioxide wherein said moldings:

a) have a pore volume of 1.31 to 1.8 ml/g; and b) are made by a process in which $SiO_2$ is compounded and shaped in the absence of a binder containing an inorganic constituent.

2. A supported catalyst for the production of vinyl acetate monomer (VAM) which contains, on a support, as catalytically active components, at least one member selected from the group consisting of palladium, palladium compounds and palladium alkali metal compounds optionally together with at least one member selected from the group consisting of gold, gold compounds, cadmium, cadmium compounds, barium, barium compounds and palladium together with at least one member selected from the group consisting of alkali metal compounds and at least one member selected from the group consisting of gold, cadmium and barium, and wherein the support comprises a molding in accordance with claim 1.

3. A process for preparing a supported catalyst according to claim 2 for the production of vinyl acetate monomer comprising:

- soaking, spraying, moistening, immersing or precipitating the palladium, gold, cadmium and barium, metal compounds,
- optionally reducing reducible metal compounds applied to the support,
- washing to remove any optionally present chloride,
- impregnating with alkali metal acetates or alkali metal compounds which are completely or partly converted into alkali metal acetates under reaction conditions for production of the vinyl acetate monomer.

4. A process for preparing a supported catalyst according to claim 2 for the production of vinyl acetate monomer, comprising:

- impregnating a support with (a) a basic solution and (b) a solution containing gold and palladium salts, wherein impregnation with (a) and (b) may take place at the same time or in sequence, with or without intermediate drying,
- washing the support to remove optionally present chloride,
- reducing insoluble compounds precipitated on the support before or after the washing step,
- drying catalyst precursor obtained, and
- impregnating with alkali metal acetates or alkali metal compounds which are completely or partly converted into alkali metal acetates under reaction conditions for the production of the vinyl acetate monomer,
- wherein the support for the catalyst is a molding comprising pyrogenic silicon dioxide having a pore volume of 1.31 to 1.8 ml/g.

5. A supported catalyst according to one of claim 3 or 4, wherein the alkali metal acetate or alkali metal compound is potassium acetate.

6. The supported catalyst according to claim 2 that contains a Pd/alkali metal/Au system on a support, as catalytically active component.

7. The supported catalyst according to claim 2 that contains a Pd/alkali metal/Cd system on a support, as catalytically active component.

8. The supported catalyst according to claim 2 that contains a Pd/alkali metal/Ba system on a support, as catalytically active component.

* * * * *